United States Patent
Wu et al.

(10) Patent No.: US 10,786,569 B2
(45) Date of Patent: Sep. 29, 2020

(54) LITHOGRAPHICALLY DEFINED NANOPARTICLES FOR MICROWAVE ABSORPTION

(71) Applicants: Wei Wu, Palo Alto, CA (US); Yifei Wang, Los Angeles, CA (US); Mahta Moghaddam, Los Angeles, CA (US); John Stang, South Pasadena, CA (US)

(72) Inventors: Wei Wu, Palo Alto, CA (US); Yifei Wang, Los Angeles, CA (US); Mahta Moghaddam, Los Angeles, CA (US); John Stang, South Pasadena, CA (US)

(73) Assignees: Wei Wu, Palo Alto, CA (US); Yifei Wang, Los Angeles, CA (US); Mahta Moghaddam, Los Angeles; John Stang., South Pasadena ( * ) Notice: Subject to any disclaimer, the term of this patent is extended or adjusted under 35 U.S.C. 154(b) by 68 days.

(21) Appl. No.: 15/224,562

(22) Filed: Jul. 31, 2016

(65) Prior Publication Data
US 2017/0209578 A1   Jul. 27, 2017

Related U.S. Application Data

(60) Provisional application No. 62/199,909, filed on Jul. 31, 2015.

(51) Int. Cl.
| | | |
|---|---|---|
| *A61K 41/00* | (2020.01) | |
| *A61K 9/51* | (2006.01) | |
| *A61K 9/50* | (2006.01) | |
| *A61N 5/02* | (2006.01) | |

(52) U.S. Cl.
CPC ........ *A61K 41/0052* (2013.01); *A61K 9/5031* (2013.01); *A61K 9/5115* (2013.01); *A61N 5/025* (2013.01)

(58) Field of Classification Search
None
See application file for complete search history.

(56) References Cited

U.S. PATENT DOCUMENTS

| | | | | |
|---|---|---|---|---|
| 2011/0034916 A1* | 2/2011 | Te | ......................... | A61K 9/0009 606/33 |
| 2013/0148194 A1* | 6/2013 | Altug | ................... | G01N 21/554 359/350 |
| 2013/0177523 A1* | 7/2013 | Ghandehari | ....... | A61K 41/0052 424/78.27 |
| 2015/0157713 A1* | 6/2015 | Peyman | ............. | A61K 41/0052 600/411 |

FOREIGN PATENT DOCUMENTS

| | | | | |
|---|---|---|---|---|
| WO | WO-0158458 A1 * | 8/2001 | ............. | A61K 41/00 |
| WO | WO-2007030698 A2 * | 3/2007 | ........... | A61K 9/5115 |

OTHER PUBLICATIONS

Ghahremani, P.H., et al., "Efficacy of microwave hyperthermia and chemotherapy in the presence of gold nanoparticles: An in vitro study on osteosarcoma" Int. J. Hyperthermia, pp. 625-636 (Year: 2011).*
Watts, C.M., et al., "Metamaterial Electromagnetic Wave Absorbers" Adv. Opt. Mater., pp. OP98-OP120 (Year: 2012).*
Cherukuri, P., Glazer, E. S., & Curley, S. A. (2010). Targeted hyperthermia using metal nanoparticles. Advanced drug delivery reviews, 62(3), 339-345.
Larken E. Euliss, Julie A. DuPont, Stephanie Gratton and Joseph DeSimone. "Imparting size, shape, and composition control of materials for nanomedicine." Chem. Soc. Rev., 2006, 35, 1095-1104.

* cited by examiner

*Primary Examiner* — Michael G. Hartley
*Assistant Examiner* — Lance W Rider
(74) *Attorney, Agent, or Firm* — Treasure IP Group, LLC

(57) ABSTRACT

A group of Hyperthermia micro/nano particles are prepared. Each nanoparticle has a first diameter between 1 micron to 50 micron and a first thickness between 100 nm to 5 micron, in a disk-like shape. The hyperthermia micro/nano particles in the present show enhanced heat properties under microwave radiation which can be used for diagnosis and therapeutic purpose in cancer treatment.

12 Claims, 6 Drawing Sheets

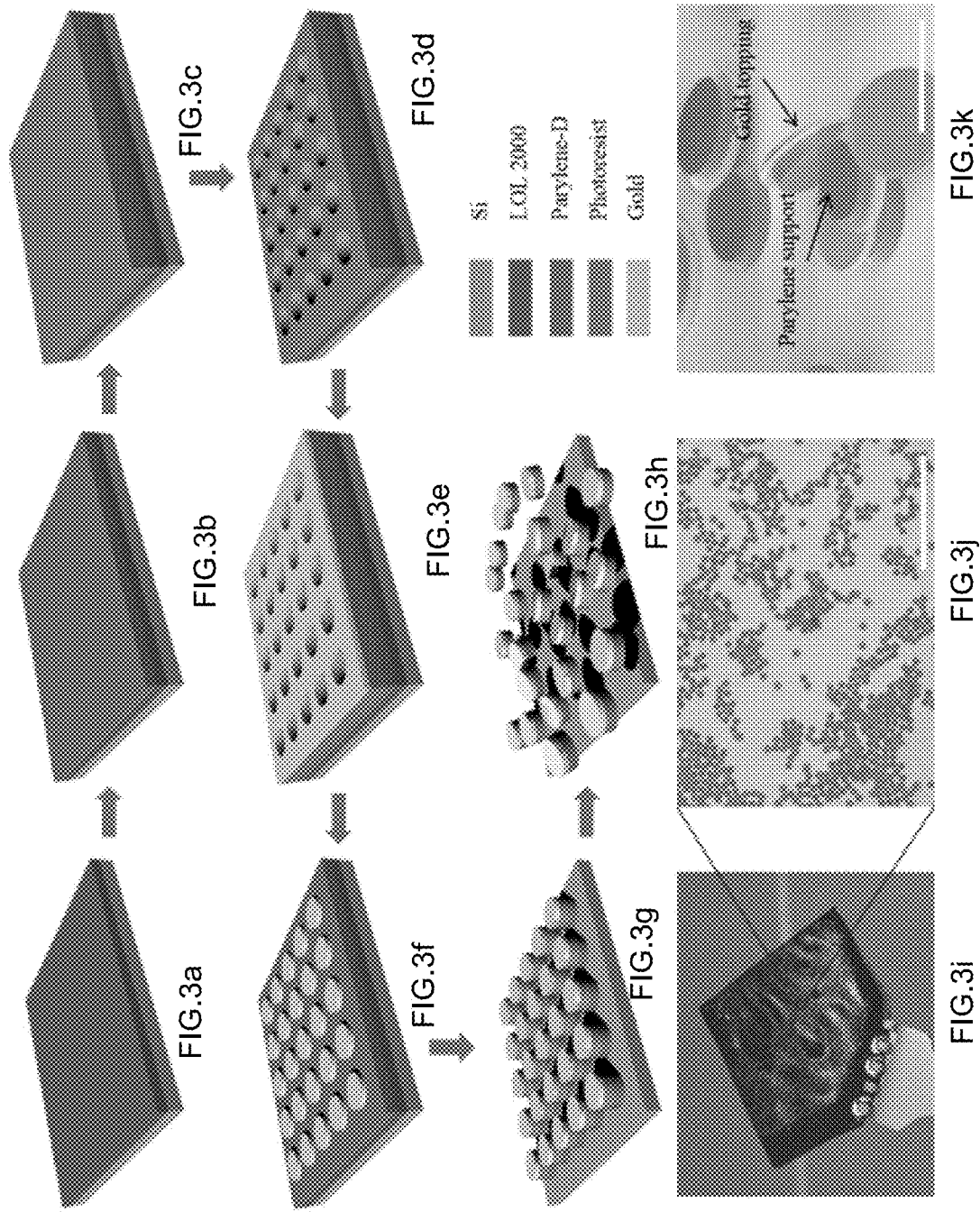

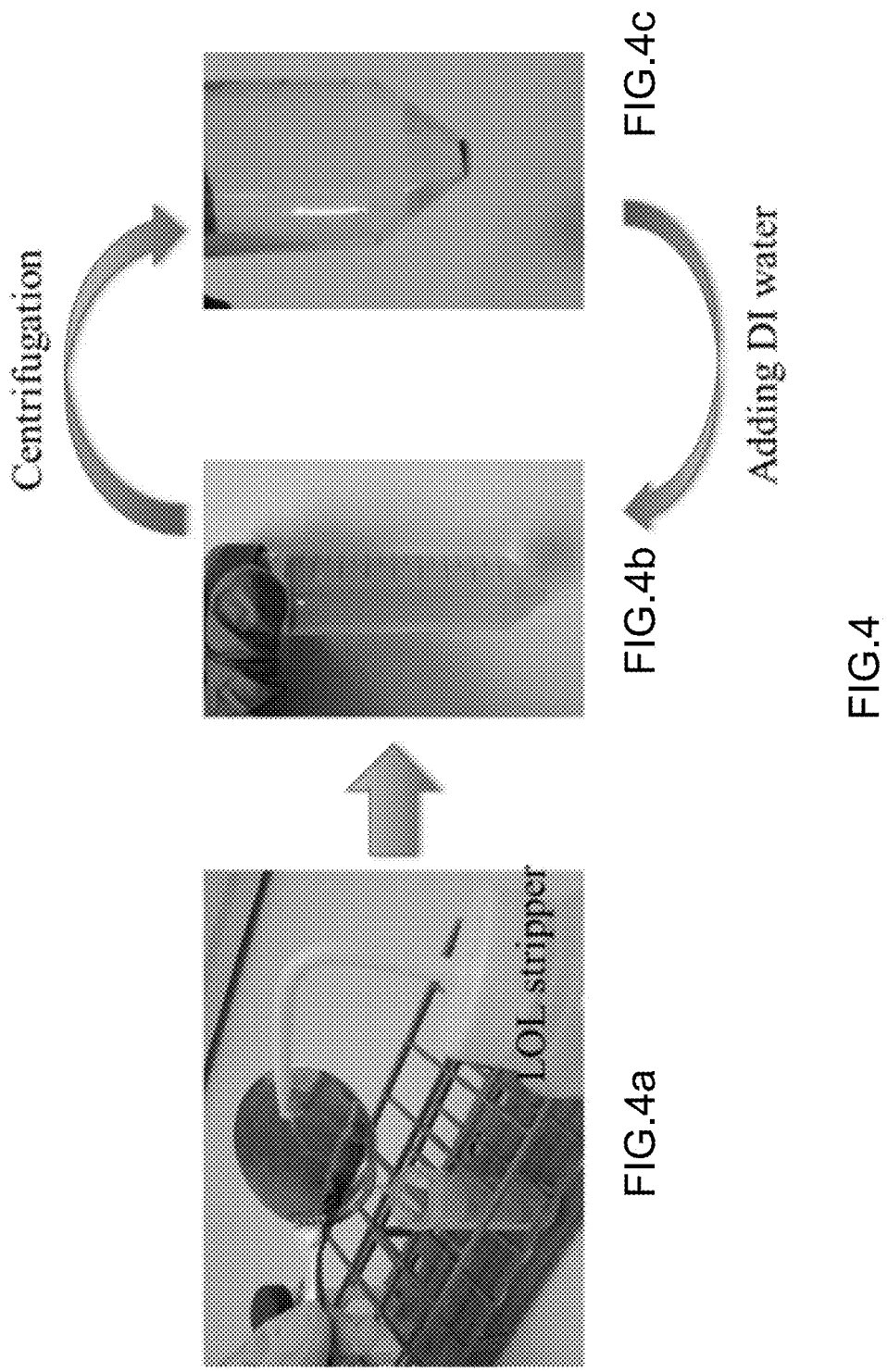

LITHOGRAPHICALLY DEFINED NANOPARTICLES FOR MICROWAVE ABSORPTION

CROSS REFERENCE TO RELATED APPLICATION(S)

The present application takes priority from a provisional application 62/199,909, filed, Jul. 31, 2015. The provisional application is herein included in its entirety.

TECHNICAL FIELD

The present invention relates to a system and method to make and use lithographically defined nanoparticles, especially in application involving microwave absorption.

BACKGROUND OF THE INVENTION

As we all know, cancer is one of the leading causes of death all over the world. The most common methods of cancer treatment include surgical resection, radio/chemotherapy, and the various combinations of them. However, surgery often fails to remove all of the cancerous cells, resulting in the regrowth of tumors. Furthermore, many tumors are inoperable because of their positions too close to critical tissues or the conditions of the patients, and radio/chemotherapy leads to many side effects.

In recent decades, there comes a promising approach called hyperthermia therapy. Researchers have found that moderate heating, in the range of 42 to 47° C., can destroy the tumor while leaving the normal tissue unaffected. This is due to the reduced heat tolerance of tumors compared to normal tissues: hyperthermia can cause apoptosis of the cells through lysis and rupture of membranes and release of digestive enzymes, leading to protein denaturation and irreversible cell damages. Compared to the common methods, Hyperthermia therapy is noninvasive and nontoxic, and has the capability of treating deep embedded tumors inside the human body.

To enhance localized heating so that the enhancement only affects tumors (so called selective hyperthermia), artificial micro/nano-particles can be injected into human bodies, accumulated around or inside tumor regions. Those particles can be high-efficiency electromagnetic wave absorbers. Then external EM fields can irradiate from outside to heat up this region in order to weaken or kill cancer cells without affecting the healthy tissues. For the current hyperthermia approaches, plasmonic photothermal therapy is a very interesting technology. Synthesized metal nanoparticles have shown to possess strongly enhanced infrared light absorption due to the phenomenon of surface plasmon resonance, leading to a heating enhancement for selective hyperthermia. However, the nanoparticles prepared by chemical synthesis have various absorption efficiency, because sometimes the chemical synthesis processes are limited by entropy, then the nanoparticles prepared by chemical synthesis have a variety of sizes and morphologies, which give nanoparticles with different absorption properties.

Therefore there is a need to make nanoparticles in more controlled process for hyperthermia related application, for cancer or other biomedical treatment.

SUMMARY OF THE INVENTION

The present invention discloses a method to make hyperthermia micro/nano particles with uniform size control and high yield and purity. The hyperthermia micro/nano particles are used together with a heating source to deliver enhanced heat for cancer treatment.

It is one object of the present invention, to manufacture micro/nano particles having high microwave absorption efficiency, to achieve the upmost heat enhancement by using the least amount of micro/nano particles or the minimal amount of injections into a patient's body.

It is another object of the present invention, to make micro/nano particles having diameters 8 µm or less. Because the micro/nano particles disclosed herein is configured to be injectable into an entire human body, sizes of the particles are therefore required to be smaller than Red Blood Cells, which are usually 8 µm in diameter.

In a first aspect of the present invention, hyperthermia micro/nano particles are disclosed. The micro/nano particles, each has a first diameter and a first thickness. Each comprises a metallic center, defined by a lithographical process, wherein the first diameter is a longest dimension of the nanoparticle and the first thickness is a dimension of the nanoparticle perpendicular to the first diameter, and the first thickness is between 100 nm to 5 micron.

In one embodiment, the first diameter is between 1 micron to 50 micron.

In another embodiment, each of the micro/nano particles further comprises a monolayer of biochemical groups formed on a surface of the nanoparticle, configured to promote adhesion to specific targets, wherein the surface extends along the direction of the first diameter.

In another embodiment, each of the micro/nano particles further comprises a monolayer of poly (ethylene glycol) (PEG) formed on a surface of the nanoparticle, configured to extend the circulation time inside human bodies, wherein the surface extends along the direction of the first diameter of each micro/nano particle.

In another embodiment, the metallic center in each of the micro/nano particles is stacked in a multi-layer structure, the multiplayer structure is having more than three metallic layers and each layer has a different metal from an adjacent layer.

In a second aspect of the present invention, a system using hyperthermia micro/nano particles is disclosed and described. The system uses a heating source. The heating source is focused beam microwave.

In one embodiment, the heating source is an external microwave irradiation, to guarantee the sufficient penetration depth into human body to reach a target diseased area.

In a third aspect of the present invention, a method to make a hyperthermia micro/nano particles is disclosed.

In a fourth aspect of the present invention, a method to use a hyperthermia micro/nano particles is disclosed and described.

DESCRIPTION OF THE DRAWINGS

FIGS. 3a-k. The fabrication and releasing processes of the disk-shaped LDPs. The results shown here were observed by naked eye, by low magnification under SEM (scale bar: 100 µm), and by high magnification under SEM (scale bar: 5 µm), respectively.

FIGS. 4a-c. Transferring the LDPs from wafers to DI water by LOL stripper flushing and multiple times centrifugation.

DESCRIPTION OF THE EMBODIMENTS

Figure 1:
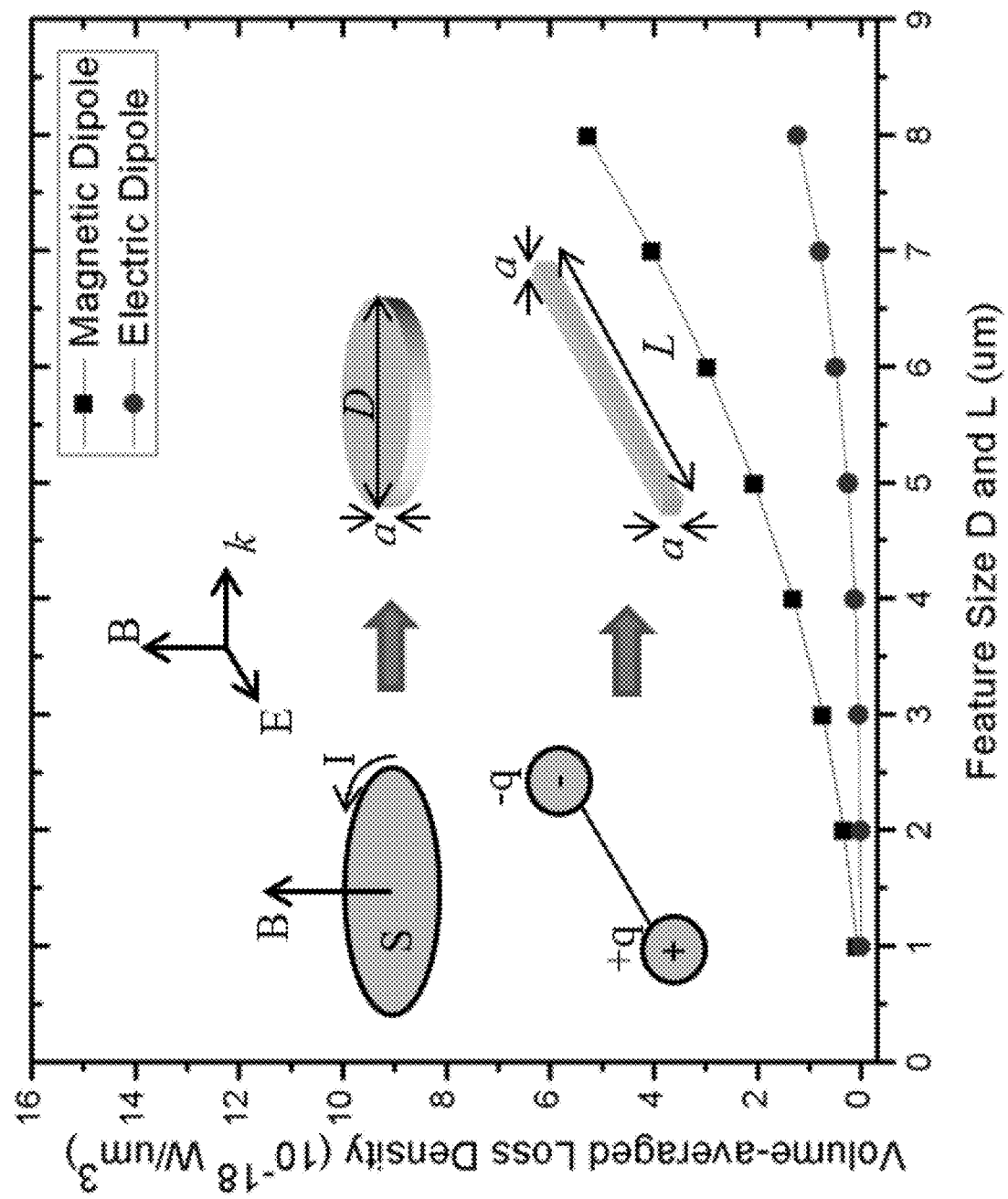
FIG. 1. Simulation results of comparison between magnetic dipoles and electric dipoles. Volume-averaged loss density versus the feature size D and L (when parameter a was 100 nm). Wherein D is diameter and L is a thickness.
Figure 2:
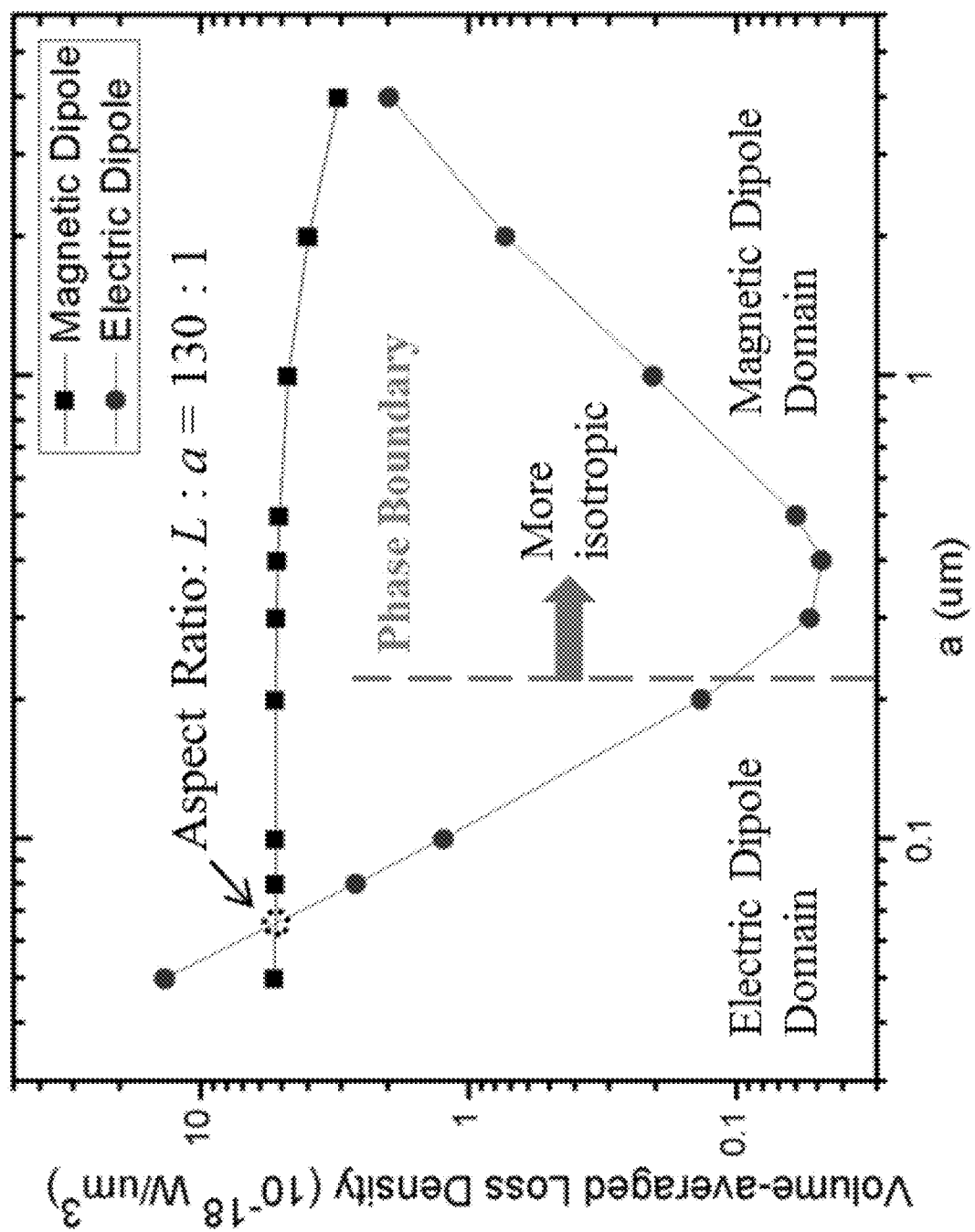
FIG. 2. Simulation results of comparison between magnetic dipoles and electric dipoles. Volume-averaged loss density versus the parameter a (when D and L were 8 µm).

Hereinafter, selected examples of a group of micro/nanoparticles and a system to be used to treat a target disease area and methods of using the same will be described in detail with reference to the accompanying drawings. The method of making the same micro/nanoparticles are also described.

For simplicity purpose, the micro/nanoparticles having a first diameter a first thickness, having an ability to enhance microwave thermal radiation and intended to be used for hyperthermia purposes are referred as hyperthermia micro/nano particles. In the present invention, the illustrated target location is an in vivo location, for example a location inside a human body, but this should not be explained as a limitation to where the hyperthermia micro/nano particles can be used. The hyperthermia micro/nanoparticles can be applied to any system that requires high microwave absorption, which includes not only for heating but also for other applications, e.g., microwave shielding or microwave isolation or insulation. Further, micro/nanoparticles can have more complex morphologies, e.g., micro LC circuit resonator, to work as microwave absorbers or scatter centers LDP is abbreviation for lithographically defined or patterned micro/nano-particles (LDPs).

In a first aspect of the present invention, hyperthermia micro/nano particles are disclosed. The micro/nano particles, each has a first diameter and a first thickness. Each comprises a metallic center, defined by a lithographical process, wherein the first diameter is a longest dimension of the nanoparticle and the first thickness is a dimension of the nanoparticle perpendicular to the first diameter, and the first thickness is between 100 nm to 5 micron.

The micro/nano particles made from a lithographically patterned micro/nano-particles (LDPs) can effectively overcome the entropy limitations of a chemical synthesis. By using top-down fabrication technology, the dimensions of the micro/nano particles can also be carefully controlled.

In the scope of the present invention, the dimension control of the micro/nanoparticles is achieved by Critical dimension (CD) control" is a term used in lithography. It measures how accurately the fabrication technology can produce certain patterns. That includes the features size offside from the design, variations from pattern to pattern and variations from run to run. In one example, the Critical dimension (CD) control is less than 0.5 micron means, the average differences between two micro/nano particles is less than 0.5 micron. In another example, the Critical dimension (CD) control is less than 0.5 micron means, the difference between longest and shortest diameter of all is less than 0.5 micron.

In one example, the first diameter of each micro/nanoparticles is between 1 micron to 50 micron. And the first diameter of each micro/nanoparticle is always longer than the first thickness of the same micro/nanoparticle.

In one instance, a single micro/nanoparticle looks substantially like a disk.

Preferably, a longest dimension of each micro/nanoparticle is less than 20 um. In a more preferred example, a longest dimension of each micro/nanoparticle is less than 15 um. In a more preferred example, a longest dimension of each micro/nanoparticle is less than 12 um. In a most preferred example, a longest dimension of each micro/nanoparticle is less than 8 um.

FIG. 1 shows a size effect on both magnetic dipoles and electric dipoles of a nanoparticle of the present invention. Both require A high-conductivity material for example a gold is used to show the size effect on magnetic dipoles and electric dipoles. As shown in this figure, magnetic dipoles can be realized by a gold disk, and electric dipoles can be realized by a gold rod. The magnetic field direction is perpendicular to the disk, while the electric field direction is parallel to the rod. The direction of the EM field is also shown on the figure. This results in the maximum absorption efficiency for both dipoles. X-axis is the feature size D and L, wherein D is diameter and L is a depth of the dielectric dipole. Y-axis is the volume-averaged loss density generated from these two types of dipoles (when parameter a was 100 nm). The structures were excited by a 1.9 GHz harmonic plane wave with electric field intensity of 1V/m. From the figure, when the feature sizes D/L increases, the volume-averaged loss density will increase. For magnetic dipoles, it is due to more magnetic flux going through the effective projection area; for electric dipoles, longer rods will result in faster movement of electrons. Therefore, in order to achieve higher loss density, larger feature sizes for both dipoles are required. But, there are limited by 8 μm.

For the effect of parameter a, (we fixed the feature size D and L to be 8 μm for both magnetic dipoles and electric dipoles), the comparison is shown in the figure above. For magnetic dipoles, the loss density will not be changed too much with a change in the thickness of the disk. However, when the thickness became comparable to the diameter of the disk, the loss density decreased. This is due to the magnetic field being screened by the sidewall of the disk (or cylinder, precisely), leading to more reflection and less penetration. However, for electric dipoles, when a is very small compared to L, loss density decreases when a increases. It is because larger a values will screen the EM field. However, when a becomes even larger, the loss density will increase. That is because larger a values provide larger projection areas from the perspective of magnetic field, therefore actually magnetic dipoles start to contribute more. In fact, there is a phase boundary of parameter a. In order to offer the same loss density, the requirement of the aspect ratio of the electric dipole should be at least 130:1. This is a very tough requirement. Moreover, we discovered that even if we change the size of the rod, the 130:1 aspect ratio is still necessary to achieve the similar loss density. This stringent requirement comes from the fact that the intrinsic impedance of gold, which is very small due to very large equivalent permittivity of gold. Compared to magnetic field intensity, the electric field intensity is too small inside gold. Therefore, disk-shaped magnetic dipoles are desired.

Optionally, each of the micro/nanoparticles, further comprises a monolayer of biochemical groups formed on a surface of the nanoparticle, configured to promote adhesion to specific targets, wherein the surface extends along the direction of the first diameter.

Additionally, each of the micro/nanoparticles, further comprises a monolayer of poly (ethylene glycol) (PEG) formed on a surface of the nanoparticle, configured to extend the circulation time inside human bodies, wherein the surface extends along the direction of the first diameter.

In one example of a preferred embodiment, each micro/nanoparticle comprises a metallic center, wherein the metallic center is stacked in a multi-layer structure, the multiplayer structure is having more than three metallic layers and each layer has a different metal from an adjacent layer. Wherein, wherein the metallic center is selected from Gold, Nickel, Cobalt, and Iron or any alloys of them.

In a second aspect of a system using hyperthermia micro/nano particles is disclosed and described. The system includes a focused beam microwave.

In one embodiment of the present aspect of the invention, the focused beam microwave is an external microwave system.

In one example, the external microwave input system using a focused microwave technology is developed in house (Stang, John, et al. "A preclinical system prototype for focused microwave thermal therapy of the breast." *IEEE Transactions on Biomedical Engineering* 59.9 (2012): 2431-2438) to further enhance the heating selectivity for local hyperthermia treatment. The system employs a 2-D array of tapered micro strip patch antennas to focus continuous-wave microwave energy in a transcutaneous manner into the desired tumor regions. Comparing with a traditional microwave input, the incident microwave will be focused into the desired tumor region, while the surrounding will be remain with little to no microwave impact.

Additionally, the focused beam microwave further comprises a photographic or visualization means to visualize or record images of the nanoparticle contrast enhanced microwave images.

In a third aspect of the present invention, a method to make hyperthermia micro/nano particles is disclosed.

The hyperthermia micro/nano particles disclosed in the present invention are very uniform, characterized by a critical dimension (CD) control parameter less than 200 nm The hyperthermia micro/nano particles can be made by patterning methods include not only photolithography, but also any of the top-down fabrication technology can be used, including but not limited to e-beam lithography, focus ion beam lithography, and nanoimprint lithography, as long as the process related critical dimension (CD) control parameter less than 200 nm. It is known by the skilled in the art that the whole of processes of top-down fabrication technology the can be scaled up in mass manufacturing.

Generally method steps to make hyperthermia micro/nano particles or aka LDPs lithographically defined or patterned micro/nano-particles, comprises the steps of
  making a patterning lithographically defined nano/micro-particles at a pre-determined size on a wafer and releasing the lithographically defined nano/micro-particles;
  collecting released lithographically defined nano/micro-particles in a solvent;
  purifying and washing the lithographically defined nano/micro-particles by centrifuge; and
  separating the lithographically defined nano/micro-particles after centrifuge by ultrasound.

The method of making the lithographically defined nano/micro-particles
  1) patterning 8-μm lithographically defined nano/micro-particles on a wafer by a conventional photolithography process on a parylene film above a sacrificial layer, wherein the parylene film is an inert layer covering the sacrificial layer to protect against all of the chemicals until a releasing step;
  2) etching using $O_2$ plasma on the parylene film and the underneath LOL layer leaving the lithographically defined nano/micro-particles as untouched; and
  3) Flushing the wafer by the LOL striper solution to dissolve the LOL layer and to release all the lithographically defined nano/micro-particles.
  4) transferring the released lithographically defined nano/micro-particles from the wafer into a DI water in a test tube and clean the lithographically defined nano/micro-particles by repeated centrifuge and addition of water until the PH 7 of the supernatant is measured as 7.

In a fourth aspect of the present invention, a method to use hyperthermia micro/nano particles is disclosed and described. The method comprising
  placing the nanoparticle inside a target area;
  providing a focused microwave beam on to the nanoparticle; and
  delivering heat enhancement to the target area through microwave absorption of the nanoparticles.

The method further comprises generating a spatially and temporally controlled thermal profile of the target area by adjusting power, shape, or relative location of the focused microwave beam radiation with respect to the position of the nanoparticle.

Figure 5A:
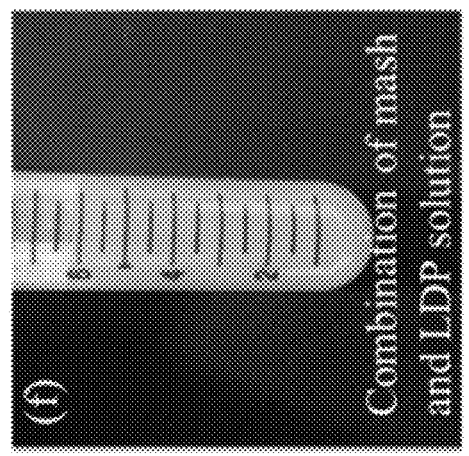
FIGS. 5a-c. Combining the agarose hydrogel mash and centrifuged LDP water solution by ultrasound mixing to obtain the particle-suspended agarose mash nanocomposite.
Figure 5B:
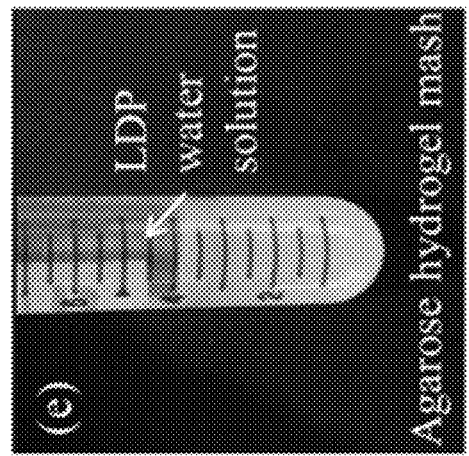
Figure 5C:
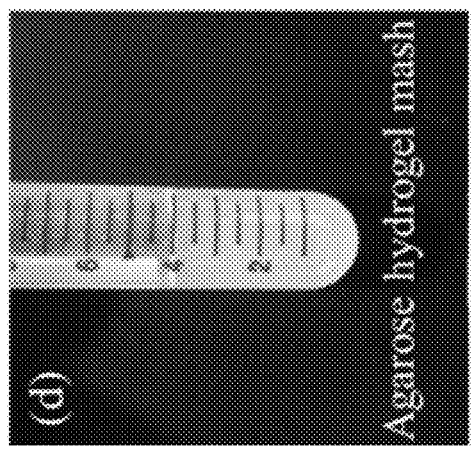
Figure 5:
Figure 6:
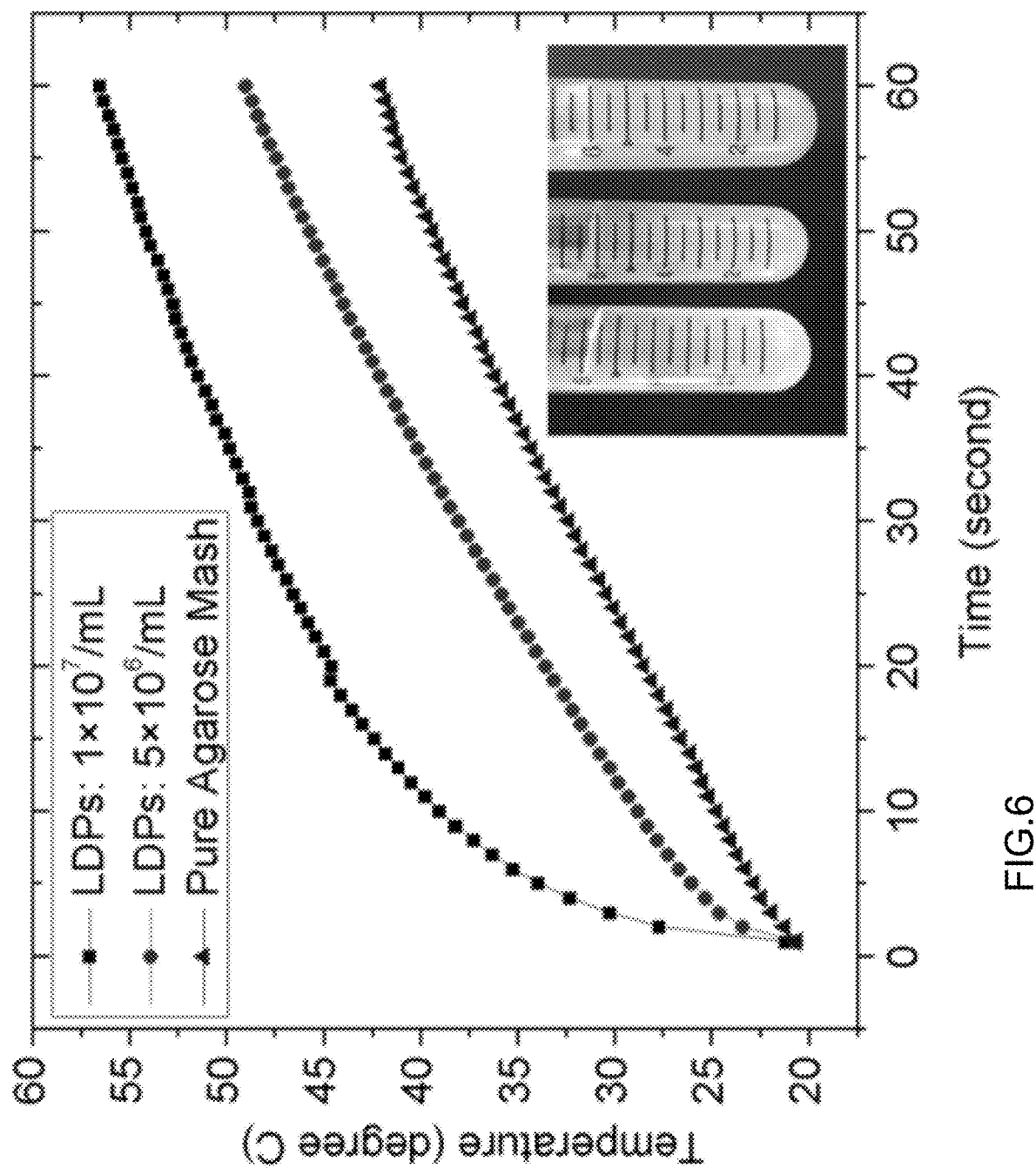
FIG. 6. Heating enhancement characterization of temperature versus time based on different LDP concentrations. The microwave input power was 20 W at 1.9 GHz.

FIG. 5 shows combining the agarose hydrogel mash and centrifuged LDP water solution by ultrasound mixing to obtain the particle-suspended agarose mash nanocomposite. FIG. 6 shows experimental results of measuring the heat enhancement. Heating enhancement characterization of temperature versus time based on different LDP concentrations. The microwave input power was 20 W at 1.9 GHz for the experimental result shown in FIG. 6.

When the hyperthermia micro/nano particles are ready to be tested, in order to closely mimic the situation that the micro/nano particle as injected and to be placed in close proximity to human tissue environments, the hyperthermia micro/nano particles were re-dispersed in to agarose hydrogel mash by ultrasound. Agarose, a jelly-like hydrogel, which is a commonly-used hydrogel in bioengineering as a matrix to mimic the human tissue environments.

FIG. 6 shows corresponding heating effects at different LDP concentrations, including a high concentration, a low concentration and a heating effect of pure agarose mash is also measured as control. It is clearly shown that addition of hyperthermia micro/nano particles can definitely improve the thermal effect with a higher concentration of the LDPs gives a larger enhancement of heating effect.

Measurement results in FIG. 6 also shows that heating occurred in two steps: an initial rapid heating step (curvature lines), followed by a gradual heating step (linear increase lines), which occurs due to intense localized heating before thermal relaxation into the surroundings. Higher concentration showed a larger difference between the initial rapid heating step and subsequent gradual heating step. The heating enhancement because of hyperthermia micro/nano particles also reduces unwanted heating in the areas that having no hyperthermia micro/nano particles.

The hyperthermia micro/nano particles disclosed herein can be further modified to achieve advanced diagnostic and therapeutic effects. The modification can be surface functionalization. The surface herein is defined as a surface of a micro/nanoparticle extends along the direction of the first diameter of the same micro/nanoparticle.

In the experiments, only the disk-shaped LDPs are demonstrated. However the it should be noted that shape of the hyperthermia micro/nano particles in fact can be fabricated in any shape and/or further optimized in new structures, alone or in combination of other nanostructures and materials, including but are not limited to, e.g., gold-nickel stacking layers, carbon nanotubes conjugation, or matching-enhanced coating. By conjugating with poly (ethylene glycol) (PEG), the circulation time of the LDPs inside human bodies can be extended.

Further hyperthermia micro/nano particles disclosed herein can be further modified to some targeting agents to enhance the specific accumulation of LDPs near tumor regions. Examples of targeting agents can be found in Cherukuri et al (Cherukuri, P., Glazer, E. S., & Curley, S. A. (2010). Targeted hyperthermia using metal nanoparticles. *Advanced drug delivery reviews*, 62(3), 339-345.

Once a cancer targeting small molecule or antibody is incorporated on to the hyperthermia micro/nano particles, the system disclosed herein can also be for cancer imaging as the hyperthermia micro/nano particles bounded tumor tissues should show significantly higher thermal profile under microwave than non-hyperthermia micro/nano particles-bounded environment or benign tissues.

In addition, these nanoparticles can be used to deliver locally enhanced chemotherapy by attaching such therapeutic agent. The combination of hyperthermia therapy and radio/chemotherapy can also be achieved by using our LDPs.

Further, themally degradable polymers or liogomer segment can be fabricated on the surface of micro/nanoparticles in the present invention, which helps to achieve a size reduction before and after microwave radiation.

Experimental Details
Preparation of 8-μm Lithographically Defined Micro/Nano-Particles Developed in Our Lab FIGS. 3 and 4 shows an exemplary fabrication and releasing process of the lithographically defined micro/nano-particles developed in our lab. First, the method comprises patterning 8-μm gold disks by a conventional photolithography process on a parylene film above a sacrificial layer of LOL 2000, wherein he parylene film is an inert layer covering the LOL 2000 layer to protect against all of the chemicals until a releasing step. Then both the parylene film and the underneath LOL layer were etched by $O_2$ plasma with the metal disks as the etching mask. Finally, the wafer was immersed into the LOL stripper solution to dissolve the LOL layer and to release all the gold micro disks. The golden disks were then characterized by low magnification under (SEM), and by high magnification under SEM. FIGS. 3*a-h* shows the fabrication and releasing processes of the disk-shaped LDPs. The results FIGS. 3*i-k* shown here were observed by naked eye, by low magnification under SEM (scale bar: 100 μm), and by high magnification under SEM (scale bar: 5 μm), respectively.

After the LDPs are released at the previous method step, the released LDPs from wafers were transferred into DI water. The LDPs were flushed out of the wafer into a testing tube by using the LOL stripper to flush the wafer. Then the test tube was put inside a centrifugation machine with 3000 rpm (1740×g) for 5 min, and all the LDPs is settled to the bottom of the test tube. The upper layer in the test tube was removed and new DI water was added into the tube to dilute the solution, then the centrifugation process was repeated again. After 6 times of dilution, the pH value of the solution was almost 7.0, and the resulted solution was effectively pure DI water. The gathered and packed LDPs are separated from each other by ultrasound agitation.

Measurement of Heat Effect of 8-μm Lithographically Defined Micro/Nano-Particles First, agarose powder (1 g) was dissolved into 100 mL hot DI water, and cooled down for network cross-linked. This jelly-like hydrogel was then ground completely by a regular blender into agarose mash. The prepared DI water-based LDPs solution was then poured into this testing tube, and one centrifugation was performed to push the LDPs to the boundary of the agarose mash and water. The upper DI water was removed from the tube to keep the total volume at 6 mL. Afterwards an ultrasound probe was used to mix the bottom agarose mash and the DI water with LDPs, leading to LDPs uniformly distributed inside the whole mixture. A last slow centrifugation (1000 rpm (193×g), 2 min) was executed to remove all the bubbles. Under such low speed centrifugation, the LDPs distribution would not change. The uniformly suspended LDPs inside this agarose mash were very stable and have not precipitated yet even after several months, perhaps because the LDPs had bonded onto pieces of the agarose mash. Moreover, the final agarose mash mixture was very viscous with much less convection compared to water. This shows that it was a good imitation of human tissue environments, and this setup could be a good mimic of the real medical situations of LDPs around/inside tumor regions.

FIG. 6 shows the heating effects at different LDP concentrations, including high concentration, low concentration and pure agarose mash. The microwave input was 20 W at 1.9 GHz. X-axis is time, and Y-axis is the temperature. It is shown that higher concentration of the LDPs provided a larger enhancement of heating effect: at 60 seconds, with the same input power of 20 W, the temperature enhancement of the high concentration case was 1.64 times of that of the pure agarose case (21.2° C. to 56.6° C. versus 20.6° C. to 42.1° C.). Experiments also showed that heating occurred in two steps: an initial rapid heating, followed by a gradual heating, which is due to intense localized heating before thermal relaxation into the surroundings. Higher concentration showed larger differences between those two steps, performing a greatly localized heating enhancement. This indicates the potential of our LDPs for localized hyperthermia treatments while minimizing heating in surrounding tissues.

We claim:
1. A system comprises
    a group of hyperthermia micro/nano particles in a target area and a means to generate focused beam microwave, wherein
        each nanoparticle, disk-shaped, is characterized by having
        a first diameter and a first thickness, comprising:
        a gold metallic center, synthesized by a lithographic process, wherein
        the first diameter is a longest dimension of the nanoparticle, which is a diameter of a circular body, between 3-50 microns, and
        the first thickness is a dimension of the nanoparticle perpendicular to the first diameter, and the first thickness is between 100 nm to 5 microns;
        wherein a difference between a longest diameter to a shortest diameter of micro/nano particles in the group is less than 0.2 microns;
    and the group of hyperthermia micro/nano particles can absorb the generated focused microwave beam and deliver heat enhancement to the target area.
2. The system of claim 1, wherein the micro/nano particles are configured to be photographed or visualized.

3. The system of claim 1, further comprising a control mechanism to generate
a spatially and temporally controlled thermal profile of the target area by adjusting power, shape, or relative location of the focused microwave beam radiation with respect to the position of the nanoparticle.

4. The system of claim 1, wherein the nano/micro-particles are purified:
using ultrasound technology to separate the nano/microparticles and using ultrasound to re-immersed in a matrix.

5. The system of claim 1 is used as a microwave shield system.

6. The system of claim 1, wherein the hyperthermia micro/nano particles further comprise a thermal degradable polymer.

7. The system of claim 1, wherein the hyperthermia micro/nano particles are synthesized by a top-down patterning method selected from photolithography, e-beam lithography, focus ion beam lithography, and nanoimprint lithography.

8. The system of claim 1 is used in a combination of radio/chemotherapy.

9. The system of claim 1, wherein the first diameter of each micro/nano particle is between 3 to 8 microns.

10. The system of claim 1, wherein each micro/nano particle further comprises
a monolayer of biochemical groups formed on a surface of each micro/nanoparticle, configured to promote adhesion to a specific target, wherein the surface of a micro/nanoparticle extends along the direction of the first diameter of the same micro/nanoparticle.

11. The system of claim 9, wherein the first thickness of each micro/nanoparticle is less than the first diameter of each micro/nano particle to be configured to minimize volume-average loss density decrease.

12. The system of claim 11, wherein when the first diameter of each micro/nano particle is 8 microns, the first thickness of the of each micro/nanoparticle is between 0.2-1 micron.

* * * * *